US 8,252,061 B2

(12) United States Patent
Mikami et al.

(10) Patent No.: US 8,252,061 B2
(45) Date of Patent: Aug. 28, 2012

(54) FEMORAL STEM FOR ARTIFICIAL HIP JOINT AND ARTIFICIAL HIP JOINT INCLUDING THE SAME

(75) Inventors: Hiroshi Mikami, Tokushima (JP); Sumihiko Maeno, Osaka (JP)

(73) Assignees: Hiroshi Mikami, Tokushima (JP); Japan Medical Materials Corporation, Osaka (JP)

( * ) Notice: Subject to any disclaimer, the term of this patent is extended or adjusted under 35 U.S.C. 154(b) by 191 days.

(21) Appl. No.: 12/084,265

(22) PCT Filed: Oct. 26, 2006

(86) PCT No.: PCT/JP2006/321328
§ 371 (c)(1),
(2), (4) Date: Aug. 7, 2008

(87) PCT Pub. No.: WO2007/052521
PCT Pub. Date: May 10, 2007

(65) Prior Publication Data
US 2009/0164026 A1 Jun. 25, 2009

(30) Foreign Application Priority Data
Oct. 31, 2005 (JP) .................. 2005-316712

(51) Int. Cl.
*A61F 2/32* (2006.01)
(52) U.S. Cl. .................. 623/23.15; 623/22.4; 606/69
(58) Field of Classification Search .... 623/22.11–22.12, 623/22.15, 22.4–22.42, 23.11, 23.15, 23.18, 623/23.21–23.29, 23.35, 23.39–23.4, 23.44; 606/64, 70, 74, 71, 283, 284, 286, 287, 280, 69
See application file for complete search history.

(56) References Cited

U.S. PATENT DOCUMENTS

| | | | | |
|---|---|---|---|---|
| 4,605,416 A | * | 8/1986 | Grobbelaar | 623/23.27 |
| 4,790,854 A | * | 12/1988 | Harder et al. | 623/20.15 |
| 5,324,291 A | | 6/1994 | Ries et al. | |
| 5,356,410 A | * | 10/1994 | Pennig | 606/62 |

(Continued)

FOREIGN PATENT DOCUMENTS
JP 6-217992 8/1994
(Continued)

OTHER PUBLICATIONS

International Search Report issued Nov. 28, 2006 in International (PCT) Application No. PCT/JP2006/321328.

*Primary Examiner* — William H. Matthews
*Assistant Examiner* — Marcia Hoffman
(74) *Attorney, Agent, or Firm* — Wenderoth, Lind & Ponack, L.L.P.

(57) ABSTRACT

A femoral stem including a stem member having a distal part of the stem member which is inserted in a medullary cavity of a femur and fixed therein and a proximal part of the stem member which has a neck for fixing an artificial head and is positioned at a proximal end of the distal part. The distal part and the proximal part are integrated or separable. Also, a plate fixing portion is detachably attached at a top of the proximal part, and a greater trochanter plate is provided for depressing the greater trochanter. The greater trochanter is fixed to the plate fixing portion at a certain angle or is fixed to the plate fixing portion so as to adjust an angle of the trochanter plate.

10 Claims, 8 Drawing Sheets

U.S. PATENT DOCUMENTS

| | | | |
|---|---|---|---|
| 5,665,088 A | 9/1997 | Gil et al. | |
| 5,797,916 A | 8/1998 | McDowell | |
| 5,824,108 A | 10/1998 | Huebner | |
| 5,906,644 A * | 5/1999 | Powell | 623/20.15 |
| 5,941,881 A * | 8/1999 | Barnes | 606/71 |
| 6,066,141 A | 5/2000 | Dall et al. | |
| 7,077,844 B2 * | 7/2006 | Michelson | 606/71 |
| 7,179,259 B1 * | 2/2007 | Gibbs | 606/64 |
| 7,207,993 B1 * | 4/2007 | Baldwin et al. | 606/70 |
| 2004/0236337 A1 * | 11/2004 | Deloge et al. | 606/74 |

FOREIGN PATENT DOCUMENTS

| | | |
|---|---|---|
| JP | 7-163581 | 6/1995 |
| JP | 8-506751 | 7/1996 |
| JP | 10-179605 | 7/1998 |
| JP | 10-337297 | 12/1998 |
| JP | 11-76280 | 3/1999 |
| WO | 94/18910 | 9/1994 |

* cited by examiner

FEMORAL STEM FOR ARTIFICIAL HIP JOINT AND ARTIFICIAL HIP JOINT INCLUDING THE SAME

BACKGROUND OF THE INVENTION

1. Field of the Invention

The present invention relates to a femoral stem for an artificial hip joint used in the treatment of transcervical fracture in the hip joint, and an artificial hip joint that includes the same, particularly to a femoral stem having a greater trochanter plate disposed at the top of the femoral stem and an artificial hip joint that includes the same.

2. Description of the Related Art

A femur of an elderly person is often weakened due to progressed osteoporosis. As a result, when the femur of the elderly person is subjected to an external force that is not normally experienced due to falling down or other incidents, the femur may be broken in the neck of the proximal part of the femur. Such a fracture is referred to as transcervical fracture. The transcervical fracture is classified into an intracapsular fracture and an extracapsular fracture by the position where the fracture occurs, whether it is inside or outside of the joint capsule. The intracapsular fracture and the extracapsular fracture require different methods of treatment.

The extracapsular fracture is treated with a surgical operation that secures the head of femur and the femur by means of an internal fixation tool (CHS, nail, etc.) in anticipation of the coaptation of the bone. In case severing of the greater trochanter is involved, a treatment of securing the greater trochanter onto the femur is also carried out by using a greater trochanter plate. The greater trochanter plate is disposed on the outer surface of the greater trochanter and is fastened while being pressed toward the femur by means of a wire or the like, so that the greater trochanter is secured onto the femur.

In the case of the intracapsular fracture, on the other hand, there is a possibility of a blood vessel that serves the head of femur to have been cut off and causing necrosis of the head of the femur, and therefore a surgery to replace the head of femur with an artificial femur head is carried out. The replacement surgery includes such a technique as the greater trochanter is once severed so as to remove the head of femur and replace it with a femoral stem having an artificial head of femur, and the greater trochanter that has been severed is secured at the original position (Chanley technique). The greater trochanter that has been severed is secured by using the greater trochanter plate, similarly to the case of the extracapsular fracture described above.

The conventional greater trochanter plates that have been used include such forms that are called the plate or bone grip as disclosed in Japanese Unexamined Patent Publication (Kokai) No. 6-217992 and Japanese Unexamined Patent Publication (Kokai) No. 11-76280. These greater trochanter plates are both formed in a configuration that fits to the curved exterior surface of the greater trochanter and has a plurality of through holes through which a cable is passed. These greater trochanter plates are used such that the greater trochanter plate is disposed on the outside of the greater trochanter, a wire is passed through a through hole formed in the greater trochanter plate and through a hole, that has been formed in a lesser trochanter of the femur in advance, and is wound around the femur before being clamped. Thus the greater trochanter is secured onto the femur.

Another form of the greater trochanter plate is disclosed in Japanese Unexamined Patent Publication (Kokai) No. 10-179605 that describes a holding member to be used together with a femoral stem that has an artificial head of femur. The holding member is fixed after inserting the femoral stem into the femur and securing it therein. The holding member has wires attached on both sides of the holding member. The holding member is disposed on the outer surface of the greater trochanter, and is secured by winding the wires on both sides around the femur. At this time, the wires cross the femoral stem and are guided in a predetermined direction by a notch formed in the femoral stem, so as to be wound around the femur and secured.

The conventional treatment for extracapsular fracture is based on osteosynthesis. To achieve assimilation of a bone suffering from extracapsular fracture, firm fixation is an important factor as in the case of osteosynthesis for the other part of the bone. The extracapsular fracture is divided into a stable type and an unstable type from the view point of the stability of reduction. In the stable type such as fracture in the horizontal plane, fixation can be achieved relatively satisfactorily, and therefore it is permissible to apply a load to the fractured bone at an early state in the case of some surgical techniques. However, post-surgery recovery may often be unsatisfactory in elderly patients who have weakened bones. In the unstable type such as comminuted fracture of proximal femur accompanied by the fracture of the greater trochanter and/or lesser trochanter, it is very difficult to fix and therefore the fractured part must be relieved of load over a long period of time in order to prevent the bone from again suffering dislocation under load. With such a background, it is difficult for the patient to leave the sickbed and start walking in the early stage of recovery after surgery for the treatment of transcervical fracture, and there is little hope of keeping dementia from progressing and improving the QOL (quality of life). Thus the present-day requirements in the medical field are not yet satisfied.

In the treatment of extracapsular fracture and intracapsular fracture that require the greater trochanter to be fixed, the greater trochanter plate is secured onto the femur with wire thereby holding the greater trochanter on the outside of the femur. Since the holding force is applied in the horizontal direction, it is difficult to offset the force of the gluteus medius musculus that adheres to the greater trochanter and pulls up the greater trochanter. As a result, when the gluteus medius musculus repetitively pulls up the greater trochanter, the greater trochanter plate cannot resist the force of the gluteus medius musculus pulling up the greater trochanter and eventually it becomes impossible to secure the greater trochanter at a predetermined position of the femur thus allowing the greater trochanter to be displaced upward. Furthermore, there has been a possibility of the wire breaking, thus making it necessary to perform additional surgery.

The greater trochanter plate disclosed in Japanese Unexamined Patent Publication (Kokai) No. 6-217992 and Japanese Unexamined Patent Publication (Kokai) No. 11-76280 are secured by forming a through hole for passing wire in the lesser trochanter of the femur. However, many of the patients who suffer from fracture in the head of the femur are elderly people with weak bones. Boring a hole in the femur of such an old patient often causes a secondary fracture.

SUMMARY OF THE INVENTION

Accordingly, an object of the present invention is to provide a femoral stem for an artificial hip joint that is capable of firmly securing the greater trochanter and is suitable for treatment of transcervical fracture that requires the greater trochanter to be fixed, and an artificial hip joint that includes the same.

A femoral stem of the present invention comprises a stem member including a distal part of the stem member which is inserted in a medullary cavity of a femur and fixed therein and a proximal part of the stem member which has a neck for fixing an artificial head and is positioned at a proximal end of the distal part. The distal part and the proximal part are integrated or separable, and a plate fixing portion is detachably attached at a top of the proximal part. Also, a greater trochanter plate is provided for depressing a greater trochanter. The greater trochanter plate is fixed to the plate fixing portion at a certain angle or fixed to the plate fixing portion so as to adjust an angle.

An artificial hip joint of the present invention comprises a femoral stem including a stem member including a distal part of the stem member which is inserted and fixed in the medullary cavity of a femur and a proximal part of the stem member which has a neck for fixing an artificial head and is positioned at a proximal end of the distal part. The distal part and the proximal part are integrated or separable. A plate fixing portion is detachably attached at a top of the proximal part, and a greater trochanter plate for depressing a greater trochanter is fixed to the plate fixing portion at a certain angle or fixed to the plate fixing portion so as to adjust an angle.

The artificial head is fixed to the neck of the proximal part; and a cup is fixed in an acetabulum of a pelvis and receives the artificial head so as to compose a hip joint.

In the artificial hip joint and the femoral stem of the present invention, since the greater trochanter plate is secured onto a femoral stem via the plate fixing portion, the greater trochanter can be secured more firmly, and more stable fixation can be achieved than in the prior art case where the greater trochanter plate is secured only by wires. Moreover, since the greater trochanter plate is secured at the top of the proximal part of the stem member, the greater trochanter plate covers the top of the greater trochanter when securing the greater trochanter, so that the greater trochanter can be effectively prevented from being displaced upward by the gluteus medius musculus.

The artificial hip joint and the femoral stem of the present invention are designed on the assumption that the proximal part of a femur including the head of the femur is excised and is replaced by an artificial head of femur. As a result, the present invention makes it unnecessary to have a period of forced rest for the preservation of the head of femur, or to reduce the period far shorter than in the case of osteosynthesis. Also because the greater trochanter plate has a high securing strength, it allows the patient to leave the sickbed and start walking before the greater trochanter, which has been severed, coapts. Thus the femoral stem of the present invention is capable of shortening the load-relieved period for the hip joint and enables the patient to leave the sickbed and start walking in the early stages of recovery.

The artificial hip joint and the femoral stem of the present invention can be used in the reworking replacement surgery for intracapsular fracture and extracapsular fracture of the neck of the femur and one accompanied by a defect in the proximal part of the femur. The artificial hip joint and the femoral stem are particularly suited to transcervical fracture that requires the greater trochanter to be fixed. The femoral stem of module construction where the proximal part of the stem member and the distal part of the stem member can be separated allows the distal part of the stem member to be selected in accordance with the patient's condition, and is suited to the reworking replacement surgery.

In general it is better to preserve the head of the femur when treating the extracapsular fracture, and replacement with an artificial femur head has not been practiced. However, from the view point of maintaining the comprehensive health and QOL of the patient, for example when the need to leave the sickbed and start walking in the early stages of recovery is taken into consideration for the purpose of preventing dementia from proceeding, measures for improving the post-surgery health including the replacement with an artificial head of femur should be considered. When such a stance is taken, the present invention is also suited for the treatment of extracapsular fracture.

The femoral stem of the present invention is most suitable for treating extracapsular fracture accompanied by the fracture of greater trochanter and the reworking replacement surgery for a case that involves a defect in the proximal part of the femur. As for intracapsular fracture, the stem of the present invention, provided with the greater trochanter plate, is useful for manipulation that involves severing of the greater trochanter during surgery.

BRIEF DESCRIPTION OF REFERENCE NUMERALS

Figure 1:
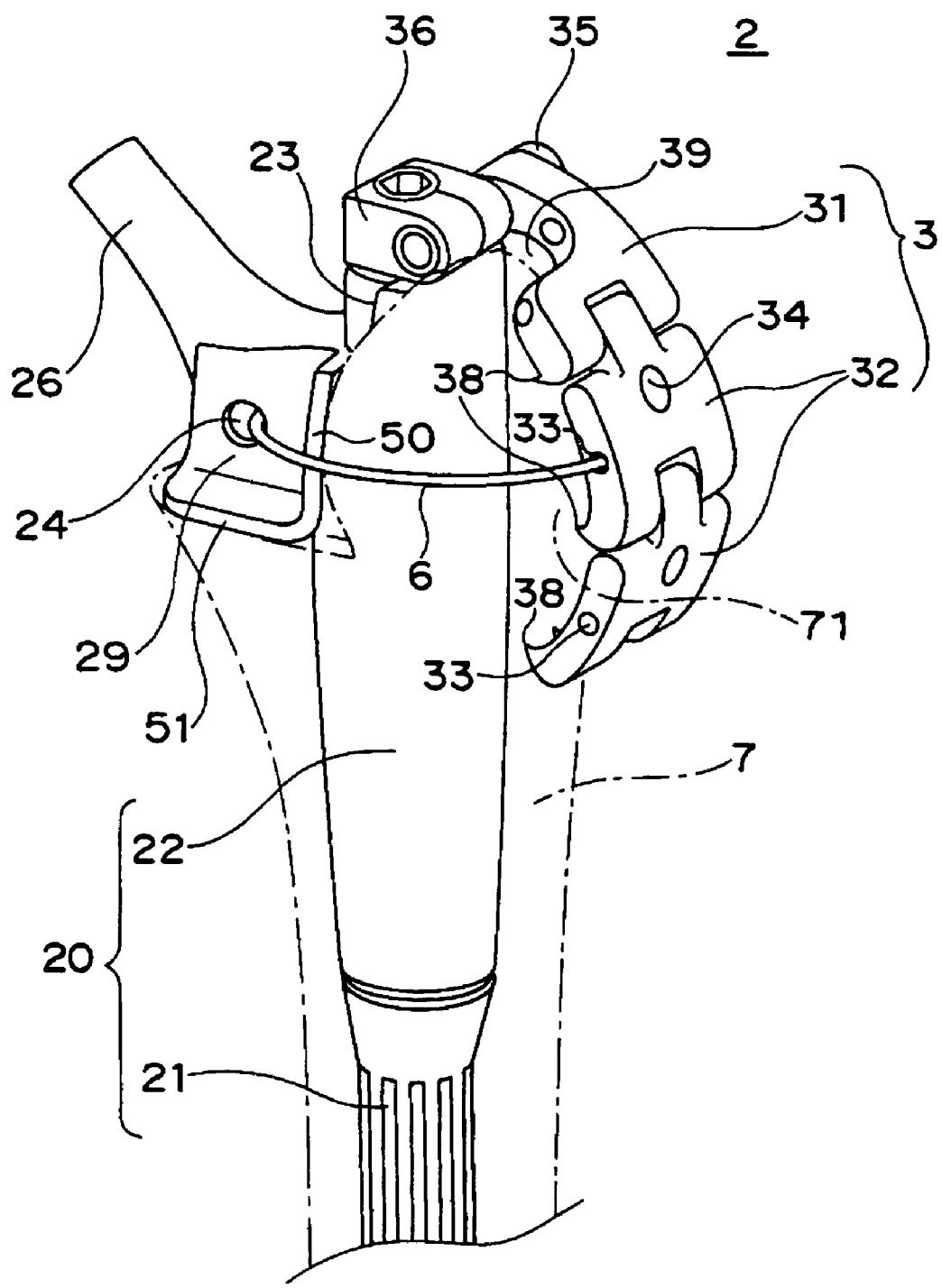
FIG. 1 is a perspective view of a femoral stem according to a first embodiment of the present invention.

1 Artificial hip joint
2 Femoral stem
21 Distal part of the stem member
22 Proximal part of the stem member
23 Top of proximal part of the stem member
24 Wire inserting opening of proximal part of the stem member
26 Neck
3 Greater trochanter plate of connected link members type
31, 32 Link members of greater trochanter plate
33 Through hole
34 Screw
36 Plate fixing portion (linkage means)
39 Clearance
4 Greater trochanter plate of integral construction
44 Claw
45 Plate setting screw
46 Plate fixing portion (linkage means)
49 Clearance
50 Rotation preventing ridge
51 Subsidence preventing ridge
6 Wire
63 Plate fixing portion (linkage means)
66 Auxiliary plate
67 Through hole of auxiliary plate
7 Femur 71 Greater trochanter
81 Artificial head of femur
91 Artificial hip joint

DETAILED DESCRIPTION OF THE PREFERRED EMBODIMENTS

Figure 8:
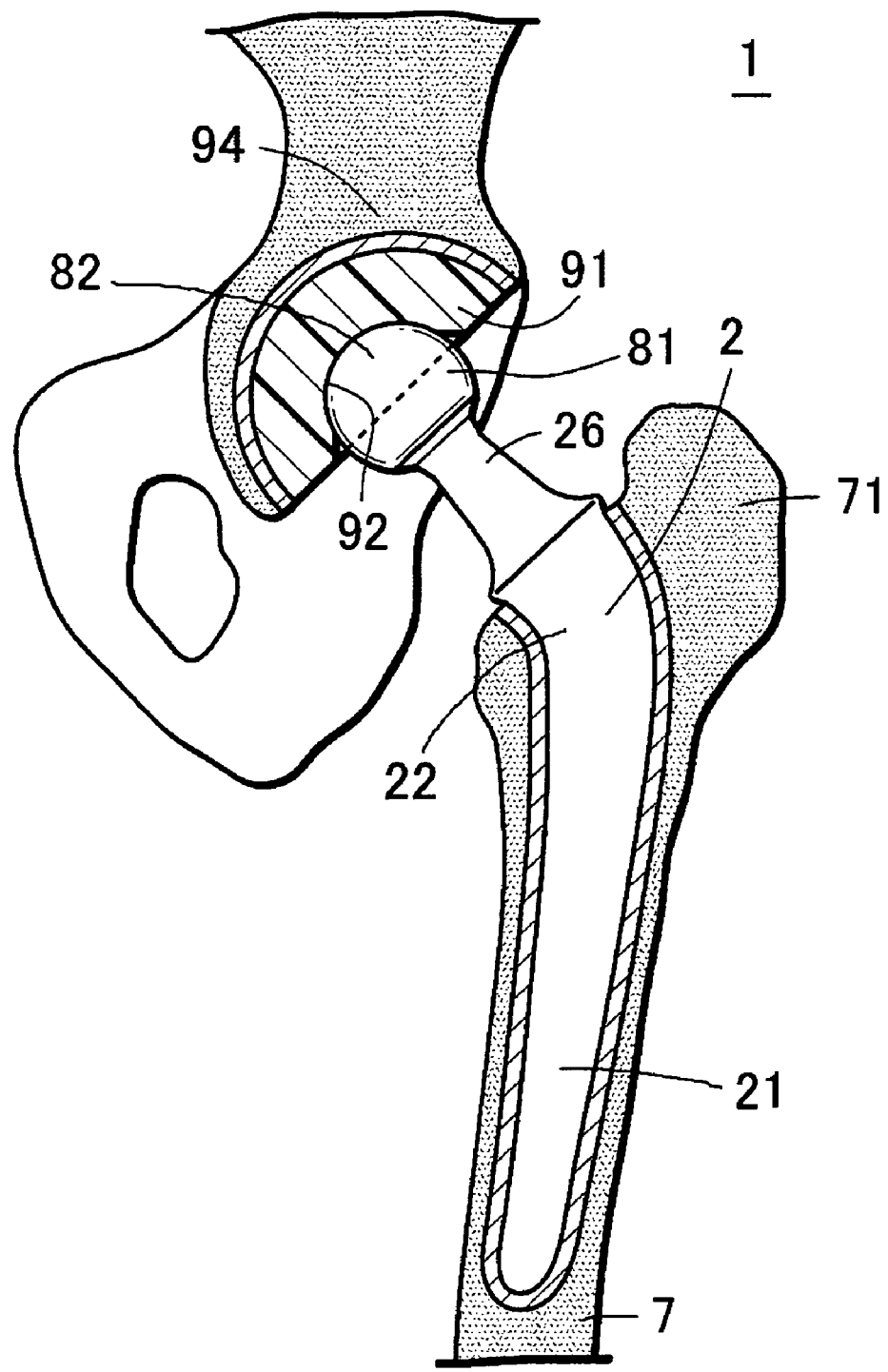
FIG. 8 is a partial sectional view showing a common artificial hip joint secured in a hip joint.

An artificial hip joint 1 is constituted roughly from a femoral stem 2 secured onto a femur 7, an artificial head of femur 81 secured onto the tip on proximal side of the femoral stem 2 and a cup 91 secured onto an acetabulum of hip bone 94 of pelvis, as shown in FIG. 8. A head of femur articular surface 82 on the surface of the artificial head of femur 81 makes slidable contact with a cup articular surface 92 inside of a recess of the cup 91 so as to constitute a joint section.

The articular surface 82 of the artificial head of femur 81 is finished so as to be very smooth. The artificial head of femur 81 is attached to the distal end of a neck 26 formed in a proximal part of the stem member 22 of the femoral stem 2. The artificial head of femur 81 is formed in a ball shape that is partially cut away, and is made of a metal having high biocompatibility such as cobalt-chrome alloy or a ceramic material such as alumina or zirconia.

The cup 91 is formed in a hollow semi-spherical shape from an ultra-high molecular weight polyethylene (UHMWPE). The articular surface 92 is an inner surface of the hollow space that receives the artificial head of femur 81 freely rotatably and is finished smoothly as the articular surface 82 of the artificial femur head 81.

The femoral stem 2 of the present invention can be used either individually or together with the cup 91. For example, for a patient who has both the acetabulum of hip bone and the head of femur damaged by a disease such as rheumatism, a combination of the cup 91 and the femoral stem 2 may be used, while only the femoral stem 2 may be used for a patient whose acetabulum of hip bone is kept in a healthy state such as in a case of transcervical fracture.

First Embodiment

The femoral stem 2 of this embodiment is constituted by a stem member 20 secured onto the femur 7, a linkage means 36 mounted at the top of the stem member 20, and the greater trochanter plate 3 secured on the stem member 20 via the linkage means 36, as shown in FIG. 1. The stem member 20 is constituted from a distal part of the stem member 21 inserted and secured in the medullary cavity of the femur 7, and a proximal part of the stem member 22 that has a neck 26 whereon the artificial head of femur 82 is mounted and is secured at the proximal end of the distal part of the stem member 21, which are separably combined.

The linkage means 36 is a plate fixing portion for securing the greater trochanter plate 3 at the top 23 of the proximal part of the stem member 22. The linkage means 36 can be removed from the proximal part of the stem member 22, and can also be used as a femoral stem that does not use the greater trochanter plate.

The linkage means 36 and the greater trochanter plate 3 are fastened to each other by means of a plate setting screw 35. The angle between the greater trochanter plate 3 and the stem member can be adjusted while the plate setting screw 35 is loosened. The greater trochanter plate 3 and the stem member can be fastened to each other by tightening the plate setting screw 35. Thus the femoral stem 2 of this embodiment allows it to freely adjust the angle of securing the greater trochanter plate 3 in accordance with the dimensions and shape of the greater trochanter 71.

The greater trochanter plate 3 is composed by linking a plurality of link members 31, 32, 32 in a band shape, and at least one of the link members 31, 32, 32 has a through hole 33 for passing a wire 6. The proximal part of the stem member 22 also has an opening 24 for inserting a wire 6 therethrough.

By constituting the greater trochanter plate 3 from a plurality of link members 31, 32, 32, it is possible to adjust the dimensions of the greater trochanter plate 3 to match the size of the greater trochanter 71 by adjusting the number of link members. Also it is possible to adapt the greater trochanter plate 3 to the external shape of the greater trochanter 71 by changing the extent of the bend of the joint between the link members.

The link members have different shapes between the link member 31 that is secured onto the proximal part of the stem member 22 and the other link members 32. The link member 31 has a clearance 39 for passing the tendon of the gluteus medius musculus.

The link members 31, 32, 32 may have spinal protrusions 38 on the front surfaces which contact the greater trochanter 71. The spinal protrusions 38 exert frictional force on the surface of the greater trochanter 71 so as to restrict sliding when the greater trochanter 71 is held by the greater trochanter plate 3.

Figure 2:
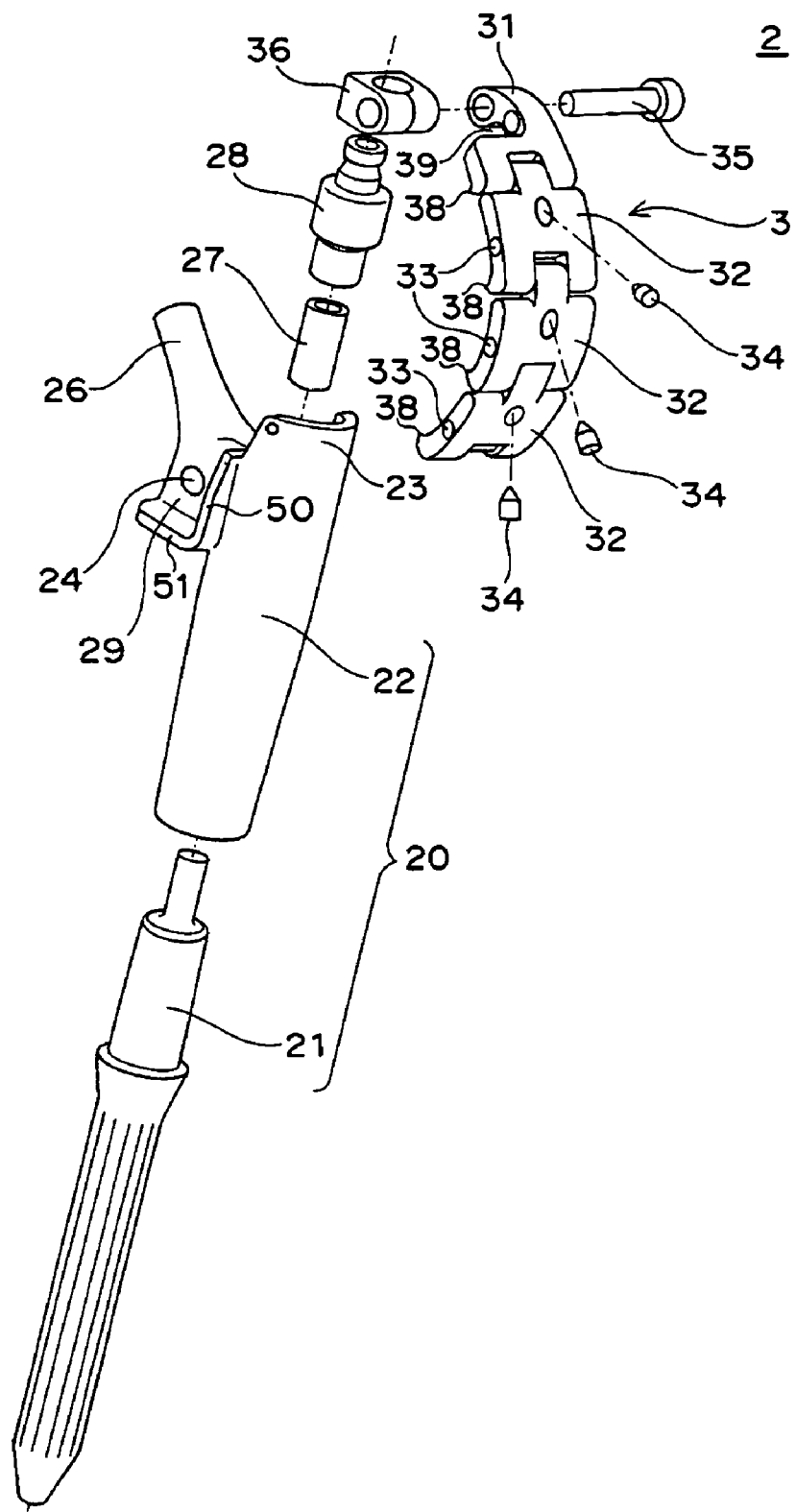
FIG. 2 is an exploded perspective view of the femoral stem according to the first embodiment of the present invention.

The stem member 20 is constituted by assembling the distal part of the stem member 21 and the proximal part of the stem member 22 which are prepared separately, as shown in FIG. 2. The proximal part of the stem member 22 has a through hole to permit assembly of the distal part of the stem member 21 and the proximal part of the stem member 22 into an integral piece by inserting the top end of the distal part of the stem member 21 into the bottom end of the through hole and inserting a distal bolt into the top end of the through hole and fastening these members by screwing in the through hole.

The stem member 20 of the modular construction as described above has such an advantage that the distal part of the stem member 21 and the proximal part of the stem member 22 can be selected in accordance with the patient's condition. The stem member 20 of the modular construction is particularly advantageous for reworking replacement surgery in which the femoral stem is fixed again in a patient whose femoral stem has been removed. Selectively using the distal part of the stem member 21 makes it easier to assemble a femoral stem that is longer than the femoral stem previously used. This makes it possible to provide a femoral stem 2 that is suited to various cases of disease while reducing the number of component parts to be kept in inventory.

The femoral stem 2 of this embodiment also has such a feature that the base portion 29 of the neck 26 is formed larger than that of the prior art femoral stem. This configuration can be preferably used in the reworking replacement surgery. In a patient who requires reworking replacement surgery because of slackness and subsidence of the femoral stem 2, partial or total defect is often found in the medial side of the proximal part of femur. In addition, the medullary cavity of the femur is enlarged and the cortical bone is thinned. It is difficult to prevent the stem from rotating relative to the femur and to achieve compatibility in the proximal part of femur by using the conventional femoral stem in such a state of the femur. With the femoral stem 2 of the present invention, in contrast, a high level of compatibility can be achieved by selecting and assembling the distal part of the stem member 21 and the proximal part of the stem member 22 that match the medullary cavities in the distal part and proximal part of the femur 7. Accordingly, it is made possible to achieve stability and rotation resistance of the femoral stem 2.

The femoral stem 2 of this embodiment further comprises rotation preventing ridges 50 that extend in the longitudinal direction and are provided before and behind the proximal part of the stem member 22 of the femoral stem 2, which are capable of effectively preventing the femoral stem from rotating in the femur.

The femoral stem 2 has a configuration in which a base 29 of the neck of the proximal part of the stem member 22 is formed to be larger and a subsidence preventing ridge 51 is formed to extend laterally below the base portion 29. This configuration enables the femur that is significantly thinned on the inside of the proximal part to bear the load. As a result, the femoral stem 2 is prevented from subsiding in the femur 7 when the femoral stem 2 is loaded, thus achieving improved supporting capability of the femoral stem 2.

While the femoral stem of this embodiment has a modular construction that combines the distal part of the stem member 21 and the proximal part of the stem member 22 of various dimensions, an integral femoral stem constituted from the distal part of the stem member 21 and the proximal part of the stem member 22 that are integrally formed may also be used in the present invention.

A cylindrical bolt 28 is inserted and secured in the hole of the proximal part of the stem member 22, and a linkage means 36 is secured at the top end of the cylindrical bolt 28 for connecting the proximal part of the stem member 22 and the greater trochanter plate 3. One end of the greater trochanter plate 3 is fixed at the linkage means 36 by the plate setting screw 35.

In this embodiment, connection of the proximal part of the stem member 22 and the greater trochanter plate 3 is achieved by using the cylindrical bolt 28 and the linkage means 36 which are fastened by means of the plate setting screw 34, although other internal fixation tools and fastening methods may also be employed.

In a surgery to secure the femoral stem 2 onto the femur 7, the distal part of the stem member 21, the proximal part of the stem member 22 and the greater trochanter plate 3 are all prepared in the assembled state, and the distal part of the stem member 21 is inserted into the medullary cavity through the distal part of the femur 7 that has been subjected to osteotomy. Then the extent of bending in the linkage section of the link members 31, 32, 32 is adjusted so that the greater trochanter plate 3 is adapted to the external shape of the greater trochanter 71. Last, the greater trochanter is firmly clamped by the greater trochanter plate 3.

The greater trochanter plate 3 is preferably secured onto the femur 7 by passing the wire 6 through the through hole 33 formed in the link member 32, as shown in FIG. 1. This because, in case the plurality of link members 31, 32, 32 of the greater trochanter plate 3 are connected to each other by means of pins or the like, either the linkage between the link members is free to swing or the link members are connected with a weak force and therefore the greater trochanter 71 cannot be fastened with the greater trochanter plate 3 only. It is made possible to secure the greater trochanter 71 at the predetermined position of the femur 7 by means of the greater trochanter plate 3, by passing the wire 6, which is passed through the link member 31, through the opening 24 of the proximal part of the stem member and winding the wire around the femur.

Thus, the one end of the greater trochanter plate 3 is secured onto the top 23 of the proximal part of the stem member 22 by means of the plate setting screw 35, and the intermediate portion or the other end of the greater trochanter plate 3 is secured onto the opening 24 of the proximal part of the stem member 22 by the wire 6. Therefore, the force applied to hold the greater trochanter 71 is distributed among the plate setting screw 35 and the wire 6. As a result, the wire 6 is subjected to a weaker load than in the case of the conventional greater trochanter plate, so that the wire 6 is less likely to be elongated or broken. Also because the greater trochanter plate 3 is located on top of the greater trochanter 71, the greater trochanter 71 can be effectively prevented from being pulled up by the gluteus medius musculus.

In the greater trochanter plate 3 constituted by linking the link members, it is also preferable that the link members can be temporarily fastened with each other after placing the greater trochanter 71 at the predetermined position. In this embodiment, the link member 32 can be fastened to the adjacent link members 32 by means of the screw 34, and the assembly can be temporarily fixed in such a form that is adapted to the external shape of the greater trochanter. This makes it possible to prevent the link members from moving and thereby causing the greater trochanter plate to be displaced, during the period from the time when the greater trochanter plate 3 is disposed on the outside of the greater trochanter to the time when it is secured by the wire 6, even when the linkage between the link members of the greater trochanter plate 3 is free to swing or the link members are connected with a weak force.

The greater trochanter plate 3 attached to the femoral stem 2 of the present invention is similar to the conventional greater trochanter plate 3 in that the greater trochanter 71 is pressed inwardly into close contact with the femur, but is significantly different in the capability to depress the top of the greater trochanter 71. When treating the greater trochanter 71 that has been severed, the greater trochanter 71 is likely to be displaced upward before healing since the greater trochanter 71 is repetitively pulled up by the gluteus medius musculus that is attached to the greater trochanter 71. According to the present invention, however, upward displacement of the greater trochanter 71 is effectively suppressed by depressing the top of the greater trochanter 71 and therefore the greater trochanter 71 that has been severed can be reliably secured at the predetermined position of the femur.

The artificial hip joint 1 including the femoral stem 2 of the present invention is capable of firmly securing the greater trochanter 71 by mechanical means without the need to bore a hole in the femur. As a result, the hip joint can be loaded within several days after the replacement surgery, thus enabling the patient to leave the sickbed and start walking in an early stage of recovery.

Second Embodiment

Figure 3:
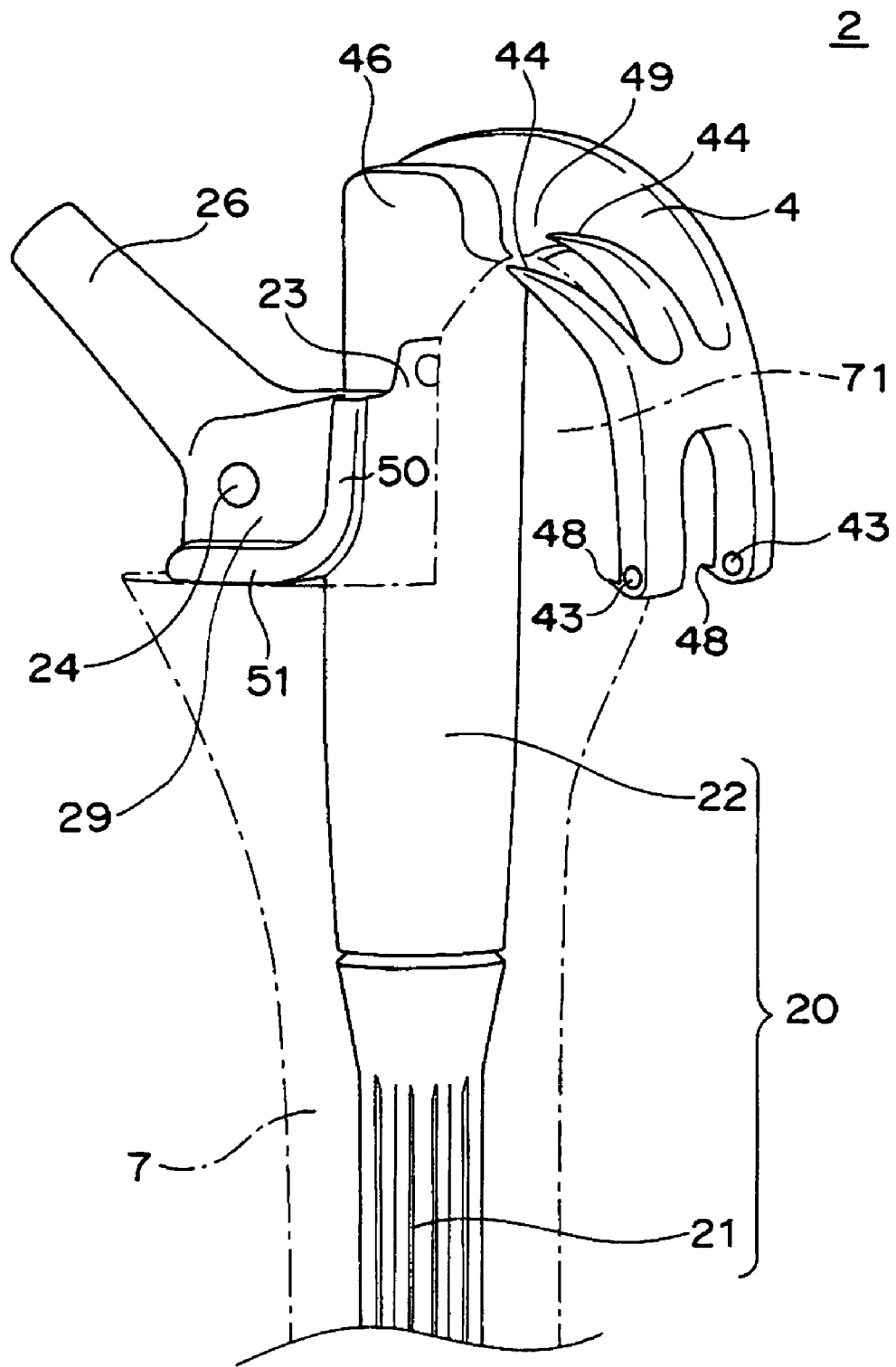
FIG. 3 is a perspective view of a femoral stem according to a second embodiment of the present invention.

The femoral stem 2 of this embodiment comprises a stem member 20 to be secured onto the femur 7, a linkage means 46 attached to the top of the stem member 20, and a greater trochanter plate 4 secured onto the stem member 20 via the linkage means 46, as shown in FIG. 3.

The stem member 20 is constituted from the distal part of the stem member 21 inserted and secured in the medullary cavity of the femur 7 and the proximal part of the stem member 22 that has the neck 26 whereon the artificial head of femur 82 is to be attached and is secured at the proximal end of the distal part of the stem member 21, which are separably combined.

The linkage means 46 is a plate fixing portion for securing the greater trochanter plate 4 on the top 23 of the proximal part 22. The linkage means 46 can be removed from the proximal part of the stem member 22, and may also be used as a femoral stem that does not employ the greater trochanter plate.

The linkage means 46 and the greater trochanter plate 4 are fastened by the plate setting screw 45. The angle between the greater trochanter plate 3 and the stem member can be adjusted while the plate setting screw 45 is loosened. The greater trochanter plate 3 and the stem member can be fastened to each other by tightening the plate setting screw 45. Thus the femoral stem 2 of this embodiment allows it to freely adjust the angle of securing the greater trochanter plate 4 in accordance to the dimension and shape of the greater trochanter 71.

The greater trochanter plate 4 is an integral plate member which has such dimensions and shape that the plate can cover an outer surface of the greater trochanter. The greater trochanter plate 4 can be replaced by loosening the plate setting screw 45, so as to select the greater trochanter plate 4 that matches the dimensions and shape of the greater trochanter 71 of the patient.

One end of the greater trochanter plate 4 is secured onto the femoral stem 2, and has a clearance 49 formed in the vicinity of the one end through which the tendon of the gluteus medius musculus bonding to the greater trochanter is passed. A claw 44 is preferably formed below the clearance 49 for hooking on the tendon of the gluteus medius musculus. The claw 44 makes the greater trochanter plate 4 less likely to move relative to the greater trochanter 71, so as to stably secure the greater trochanter 71.

Spinal protrusions 48 may also be formed on the front surface of the greater trochanter plate 4 which contacts the greater trochanter 71. The spinal protrusions 48 exert frictional force on the surface of the greater trochanter 71 so as to restrict sliding when the greater trochanter 71 is held by the greater trochanter plate 4.

Figure 4:
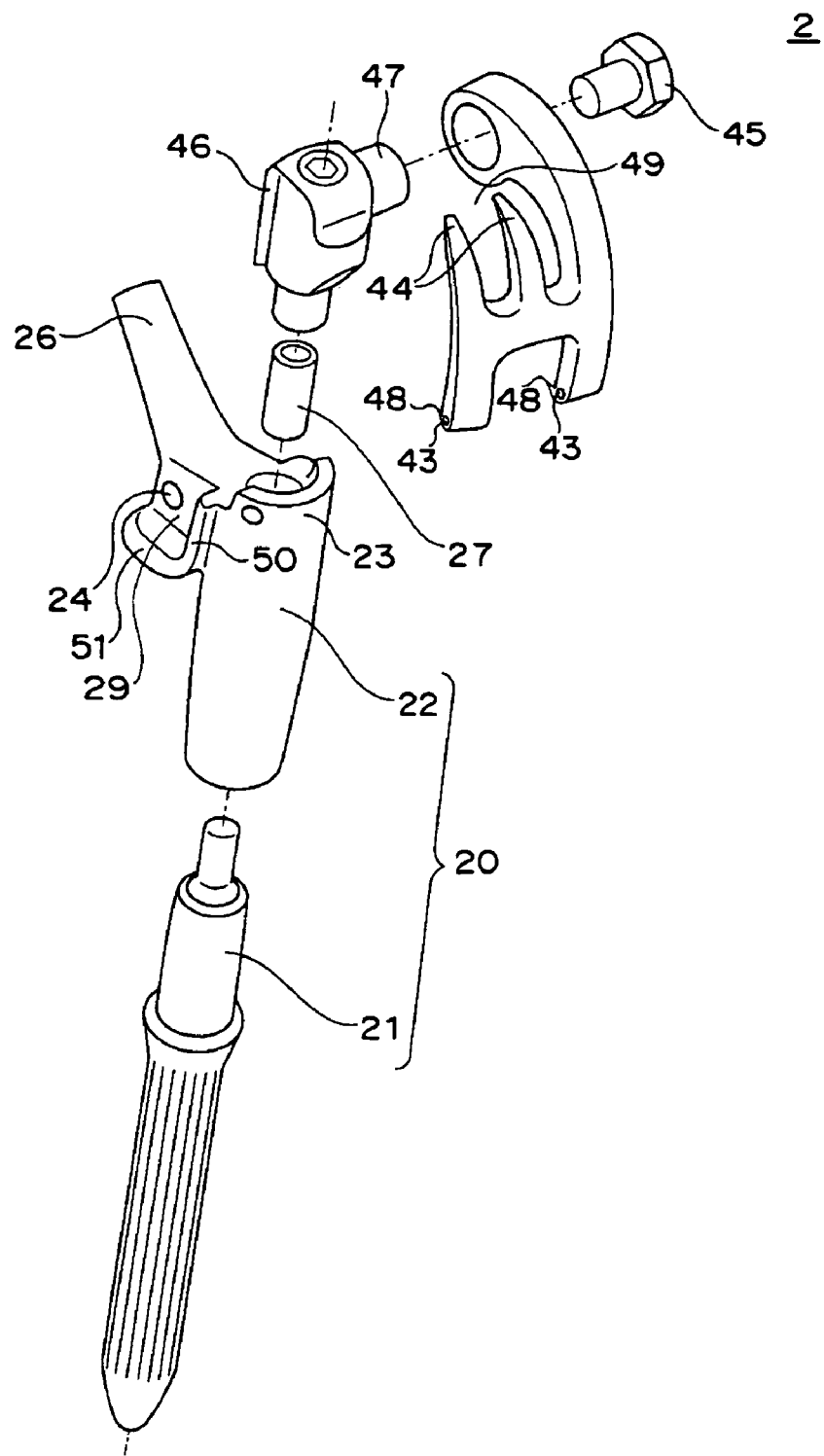
FIG. 4 is an exploded perspective view of the femoral stem according to the second embodiment of the present invention.

The stem member 20 is constituted by assembling the distal part of the stem member 21 and the proximal part of the stem member 22 which are prepared separately, as shown in FIG. 4. The proximal part of the stem member 22 has a through hole, so as to assemble the distal part of the stem member 21 and the proximal part of the stem member 22 into an integral piece by inserting the top end of the distal part of the stem member 21 into the bottom end of the through hole and inserting a distal bolt into the top end of the through hole and fastening these members by screwing in the through hole.

The stem member 20 of the modular construction as described above has an advantage in that the distal part of the stem member 21 and the proximal part of the stem member 22 can be selected in accordance with the patient's condition. The stem member 20 of the modular construction is particularly advantageous for reworking replacement surgery in which the femoral stem is fixed again in a patient whose femoral stem has been removed. Selectively using the distal part of the stem member 21 makes it easier to assemble a femoral stem that is longer than the femoral stem previously used. This makes it possible to provide a femoral stem 2 which is suited to various cases of disease while reducing the number of component parts to be kept in inventory.

The femoral stem 2 of this embodiment has a feature that the base portion 29 of the neck 26 is formed larger than that of the femoral stem of the prior art. This configuration can be preferably used in the reworking replacement surgery. In a patient who requires reworking replacement surgery because of slackness and subsidence of the femoral stem 2, partial or total defect is often found on the inner side of the proximal part of femur. In addition, the medullary cavity of the femur is enlarged and the cortical bone is thinned. It is difficult to prevent the stem from rotating relative to the femur and achieve compatibility in the proximal part of femur in such a state of the femur by using the conventional femoral stem.

With the femoral stem 2 of the present invention, in contrast, a high level of compatibility can be achieved by selecting and assembling the distal part of the stem member 21 and the proximal part of the stem member 22 that match the medullary cavity in the distal part and the proximal part of the femur 7. Accordingly, it is possible to achieve stability and rotation resistance of the femoral stem 2.

The femoral stem 2 of this embodiment further comprises the rotation preventing ridge 50 that are provided before and behind the proximal part of the stem member 22 of the femoral stem 2 to extend in the longitudinal direction, which are capable of effectively preventing the femoral stem from rotating in the femur. The femoral stem 2 has a base 29 of the neck of the proximal part of the stem member 22 that is formed to be larger and a subsidence preventing ridge 51 that is formed to extend laterally below the base portion 29. This configuration enables even the femur that is significantly thinned on the inside of the proximal part to bear the load. As a result, the femoral stem 2 is prevented from subsiding in the femur 7 when the femoral stem 2 is loaded, thus achieving improved supporting capability of the femoral stem 2.

While the femoral stem of this embodiment has a modular construction that combines the distal part of the stem member 21 and the proximal part of the stem member 22 of various dimensions, a femoral stem of an integral type constituted from the distal part of the stem member 21 and the proximal part of the stem member 22 that are integrally formed may also be used in the present invention.

The linkage means 46 is inserted and secured in the hole of the proximal part of the stem member 22, and the top end of the greater trochanter plate 4 is secured by the plate setting screw 45 onto the fitting member 47 that protrudes on the side face of the linkage means 46.

The femoral stem has high strength because of the integral construction of the greater trochanter plate 4, and is therefore capable of securing the greater trochanter 71 without using a wire. In this case, connection between the linkage means 46 and the greater trochanter plate 4 must be strong enough to resist the tension of the gluteus medius musculus. In order to achieve such a strong fastening arrangement, mechanical fitting by means of a tapered configuration is employed in this embodiment. When a cylindrical inserted portion of the plate setting screw 45 is formed in a tapered shape, and the inside of a mating portion 47 is formed as a hole having the dimension and shape that match those of the inserted portion, a strong fitting that can endure a tension exceeding 160 kg can be achieved. Instead of a taper fitting, other fitting methods may be also employed such as screwing or other mechanical fitting methods or chemical securing methods using an adhesive or the like.

In a surgery procedure to secure the femoral stem 2 onto the femur 7, the distal part of the stem member 21 and the proximal part of the stem member 22 are assembled and the greater trochanter plate 4 is temporarily rotatably secured in the proximal part of the stem member 22 in advance. Then the distal part of the stem member 21 is inserted into the medullary cavity through the distal part of the femur 7 that has been subjected to osteotomy. Then fine adjustment is made on the angle of linkage so that the greater trochanter plate 4 is adapted to the external shape of the greater trochanter 71. Last, the greater trochanter is firmly clamped by taper fitting of the greater trochanter plate 4 into the proximal part of the stem member 22.

The greater trochanter plate 4 may also have a through hole 43 for passing a wire. Similarly to the first embodiment, the wire 6 passed through the through hole 43 of the greater trochanter plate 4 can be passed through the opening 24 of the proximal part of the stem member and wound around the femur. With this constitution, since the securing force of the wire is added to the securing force of the taper fitting, stable fastening can be achieved even when the patient is heavy in weight or the gluteus medius musculus exerts a high tension.

Since the top end of the greater trochanter plate 4 is firmly secured by the plate setting screw 45 on the top 23 of the proximal part of the stem member 22, there is no need to use a wire. Even when a wire is used for an auxiliary purpose, most of the load applied for holding the greater trochanter 71 is borne by the plate setting screw 45, and therefore the wire 6 is subjected to a weaker load and the wire 6 is less likely to elongate or break. Also because the greater trochanter plate 4 is located also on top of the greater trochanter 71, the greater trochanter 71 can be effectively prevented from being pulled up by the gluteus medius musculus.

While the greater trochanter plate 4 attached to the femoral stem 2 of the present invention is similar to the conventional greater trochanter plate in that the greater trochanter 71 is pressed inwardly into close contact with the femur, it is significantly different in that the greater trochanter plate 4 holds the top of the greater trochanter 71. When treating the greater trochanter 71 that has been severed, the greater trochanter is likely to be displaced upward before healing, since the greater trochanter 71 is repetitively pulled up by the gluteus medius musculus that is attached to the greater trochanter 71. According to the present invention, however, the greater trochanter 71 is effectively suppressed from being pulled up, as the greater trochanter 71 is held by pressing on top of the greater trochanter 71, and therefore the greater trochanter 71 that has been severed can be reliably secured at the predetermined position of the femur.

The artificial hip joint 1 including the femoral stem 2 of the present invention is capable of firmly securing the greater trochanter 71 by mechanical means without the need to bore a hole in the femur. As a result, the hip joint can be loaded within several days after the replacement surgery, thus enabling the patient to leave the sickbed and start walking in the early stages of recovery.

Modification 1

Figure 5:
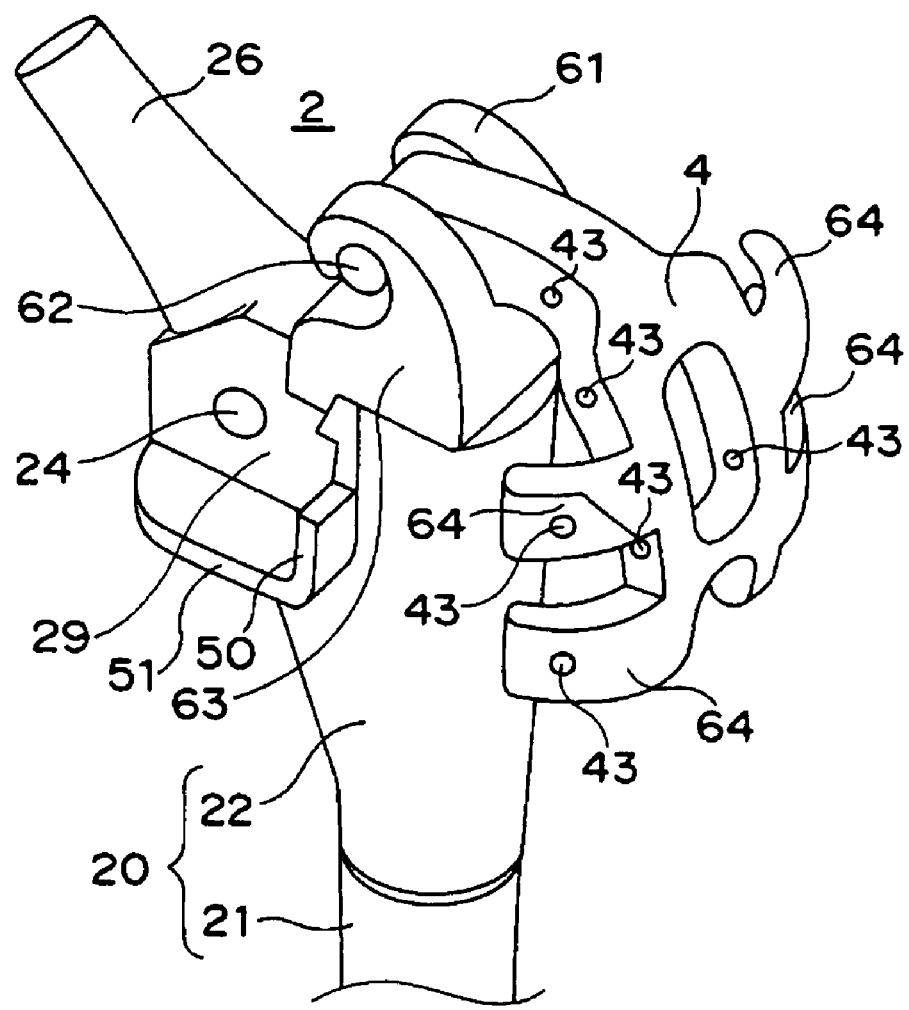
FIG. 5 is a perspective view of a femoral stem according to a modification of the present invention.

In a modification of the present invention shown in FIG. 5, the greater trochanter plate 4 of integral construction is disposed rotatably via a linkage means 63 on the proximal part of the stem member 2 of the femoral stem 2.

The linkage means 63 secured on the proximal part of the stem member 2 has a bearing section 61 that receives a shaft 62 that is formed at the top of the greater trochanter plate 4. Since the shaft 61 and the bearing section 62 can rotate relative to each other, the greater trochanter plate 4 is secured onto the greater trochanter by passing a wire through the through hole 43 formed for passing wire.

This modification, with a simple structure of connection between the greater trochanter plate 4 and the linkage means 63, enables a significant cost reduction for the femoral stem.

It is also preferable to provide wings 64 that extend laterally so as to enclose the outside of the greater trochanter as shown in FIG. 5, since this configuration makes the greater trochanter less likely to be displaced laterally.

Third Embodiment

Figure 6:
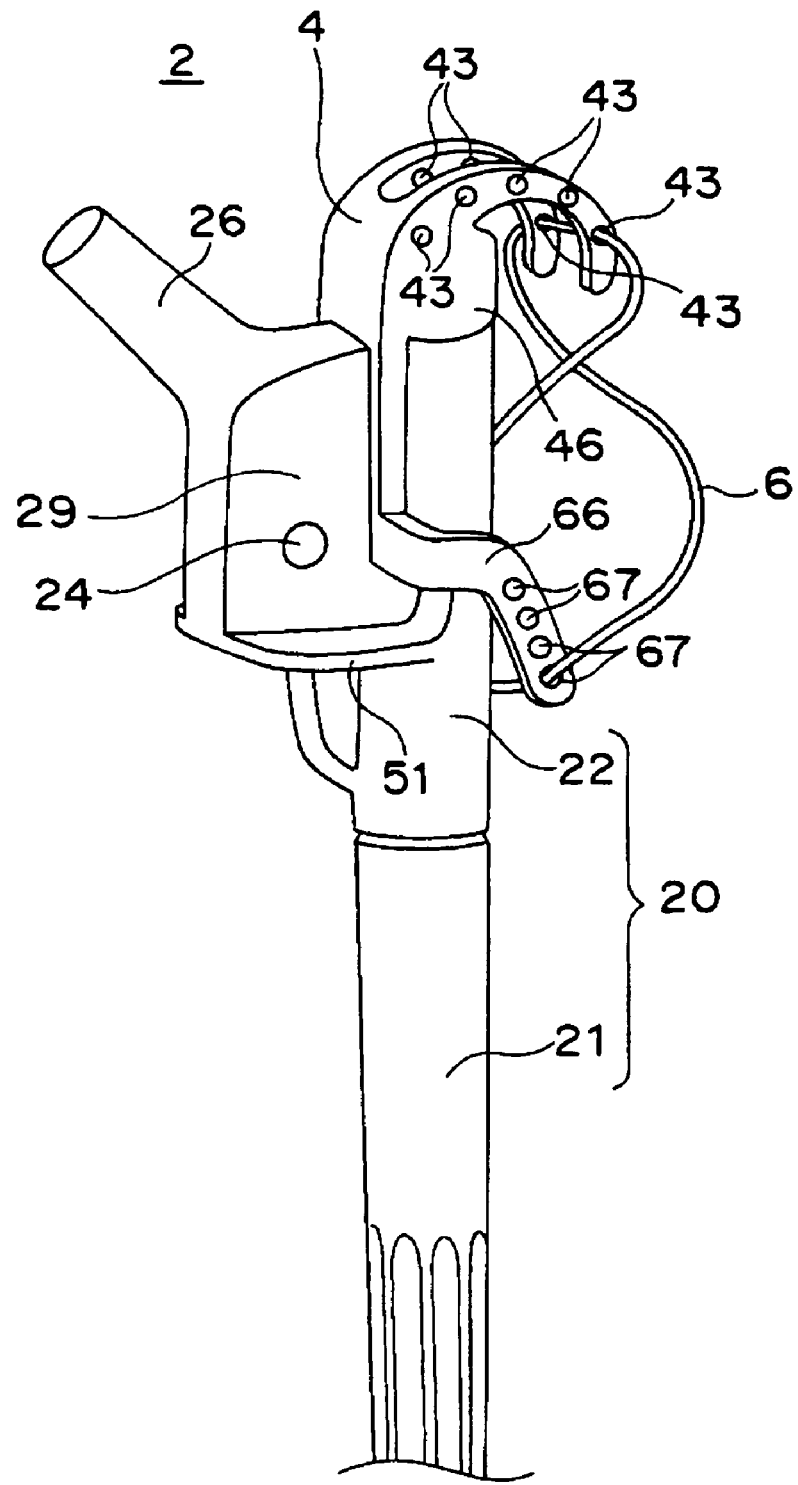
FIG. 6 is a perspective view of a femoral stem according to a third embodiment of the present invention.

The femoral stem 2 of this embodiment comprises the stem member 20 fixed in the femur 7, the linkage means 46 attached on top of the stem member 20, the greater trochanter plate 4 fixed to the stem member 20 via the linkage means 46, and at least two auxiliary plates 66 which extend from the proximal part of the stem member 22 to the right side and left side of a lower part of the greater trochanter, as shown in FIG. 6. The greater trochanter plate 4 and the auxiliary plates have through holes 43, 67, respectively, for passing a wire.

The stem member 20 is constituted from the distal part of the stem member 21 inserted and secured in the medullary cavity of the femur 7, and the proximal part of the stem member 22 that has the neck 26 whereon the artificial head of femur 82 is to be mounted and is secured at the proximal end of the distal part of the stem member 21, which are separably combined.

The linkage means 46 is a plate fixing portion for securing the greater trochanter plate 4 at the top of the proximal part of the stem member 22. The linkage means 46 can be removed from the proximal part of the stem member 22, and can also be used as a femoral stem that does not use the greater trochanter plate.

The greater trochanter plate 4 is constituted from an integral plate component formed with such dimensions and shape that cover the top surface of the greater trochanter, and is formed integrally with the linkage means 46. Therefore, in case the size of the greater trochanter plate 4 or the angle between the greater trochanter plate 4 and the stem member 20 do not match the shape of the patient's greater trochanter, the linkage means 46 may be removed from the proximal part of the stem member 22 so as to replace the greater trochanter plate 4 and the linkage means 46 with those of a more appropriate size and shape.

In this embodiment, the stem member 20 is constituted by assembling the distal part of the stem member 21 and the proximal part of the stem member 22 which are prepared separately, similarly to the first and second embodiments. The proximal part of the stem member 22 has a through hole to permit assembly of the distal part of the stem member 21 and the proximal part of the stem member 22 into an integral piece by inserting the top end of the distal part of the stem member 21 into the bottom end of the through hole and inserting a distal bolt into the top end of the through hole and fastening these members together by screwing within the through hole.

The stem member 20 of the modular construction as described above has an advantage in that the distal part of the stem member 21 and the proximal part of the stem member 22 can be selected in accordance to the patient's condition. The stem member 20 of the modular construction is particularly advantageous for reworking replacement surgery in which the femoral stem is fixed again in a patient whose femoral stem has been removed. Selectively using the proper distal part of the stem member 21 makes it easier to assemble a femoral stem that is longer than the femoral stem previously used. This makes it possible to provide a femoral stem 2 that is suited to various cases of disease while reducing the number of component parts to be kept in inventory.

The femoral stem 2 of this embodiment also has such a feature that the base portion 29 of the neck 26 is formed larger than that of the prior art femoral stem. This configuration can be preferably used in a reworking replacement surgery. In a patient who requires the reworking replacement surgery because of slackness and subsidence of the femoral stem 2, partial or total defect is often found on the inside of the proximal part of femur. In addition, the medullary cavity of the femur is enlarged and the cortical bone is thinned. It is difficult to prevent the stem from rotating relative to the femur and achieve compatibility in the proximal part of femur by using the conventional femoral stem, in such a state of the femur. With the femoral stem 2 of the present invention, in contrast, a high level of compatibility can be achieved by selecting and assembling the distal part of the stem member 21 and the proximal part of the stem member 22 that match the medullary cavities in the distal part and the proximal part of the femur. Accordingly, it is made possible to achieve stability and rotation resistance of the femoral stem 2.

The femoral stem 2 of this embodiment further comprises the rotation preventing ridges 50 that are provided before and behind the proximal part of the stem member 22 of the femoral stem 2 to extend in the longitudinal direction, so as to more effectively prevent the femoral stem from rotating in the femur.

The femoral stem 2 has a base 29 of the neck of the proximal part of the stem member 22 that is formed to be larger and a subsidence preventing ridge 51 that is formed to extend laterally below the base portion 29. This configuration enables even a femur that is significantly thinned on the inside of the proximal part to bear the load. As a result, the femoral stem 2 is prevented from subsiding in the femur 7 when the femoral stem 2 is loaded, thus achieving an improved supporting capability of the femoral stem 2.

While this embodiment employs the modular construction that combines the distal part of the stem member 21 and the proximal part of the stem member 22 of various dimensions, an integral femoral stem constituted from the distal part of the stem member 21 and the proximal part of the stem member 22 that are integrally formed may also be used according to the present invention.

In this embodiment, the greater trochanter plate 4 and the linkage means 46 that connects the greater trochanter plate 4 to the proximal part of the stem member 22 are provided as an integral piece. However, the greater trochanter plate 4 and the linkage means 46 may also be prepared separately and assembled as in the first and second embodiments.

Figure 7:
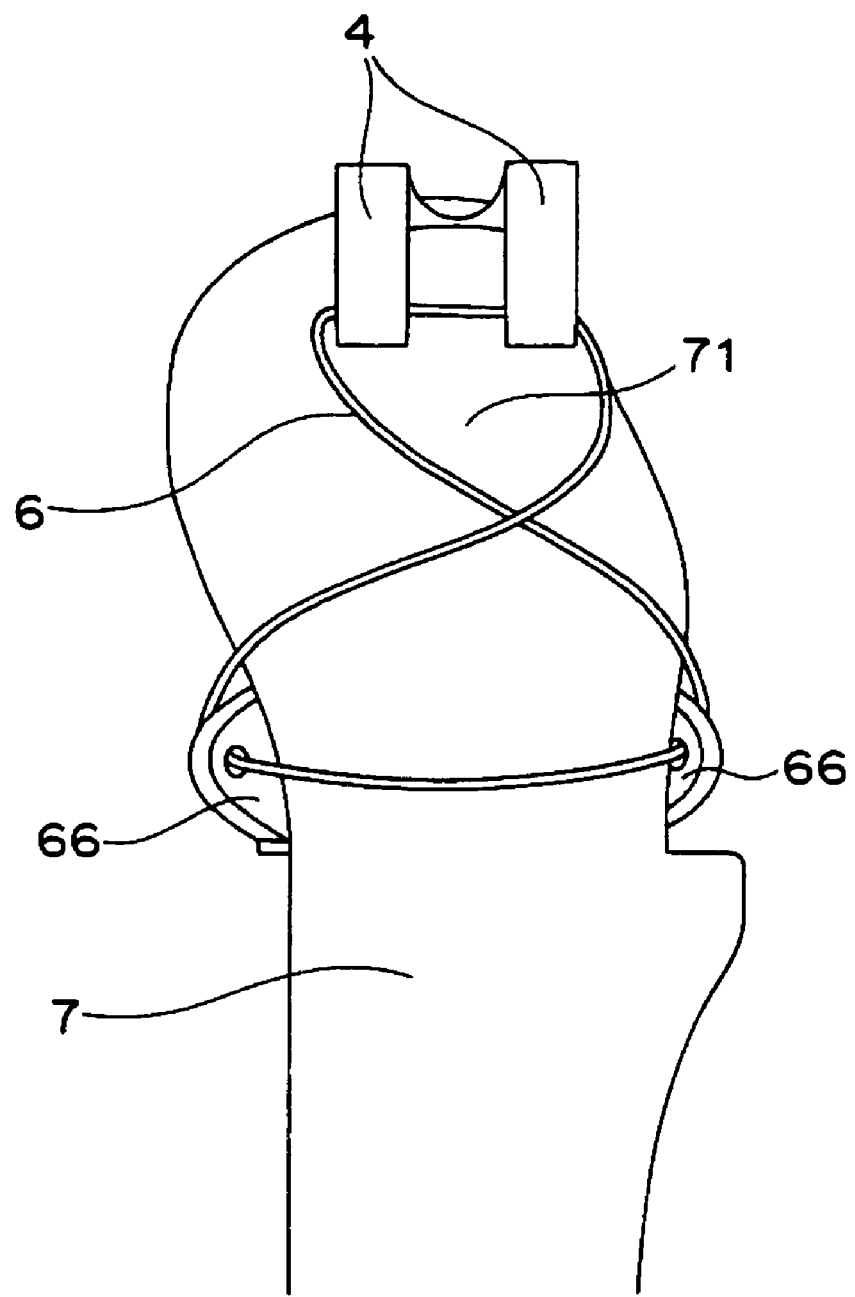
FIG. 7 is a side view of the femoral stem according to the third embodiment of the present invention as viewed from the outside.

With the femoral stem 2 of this embodiment, the greater trochanter 71 can be held on the femur 7 by running the wire 6 through the through hole 43 of the greater trochanter plate 4 and the through hole 67 of the auxiliary plate 66 as shown in FIG. 7.

In a surgery to secure the femoral stem 2 onto the femur 7, the distal part of the stem member 21, the proximal part of the stem member 22 and the greater trochanter plate 4 are prepared in the assembled state, and the distal part of the stem member 21 is inserted into the medullary cavity through the distal part of the femur 7 that has been subjected to osteotomy. Then the outside of the greater trochanter 71 is held by running the wire 6 crosswise so as to tie the greater trochanter plate 4 located above the greater trochanter 71 and the auxiliary plates 66 that extend to the right and left of the lower part of the greater trochanter together.

Thus, since the greater trochanter plate 4 is secured at the top of the proximal part of the stem member 22, it is capable of holding the top of the greater trochanter 71 so as to suppress the greater trochanter from being pulled upward. Also because the wire 6 is used to hold the greater trochanter 71 inwardly so as to secure it onto the femur 7, the wire 6 is subjected to a weaker load than in the case of the conventional greater trochanter plate, so that the wire 6 is less likely to be elongated or broken.

In this example, the greater trochanter plate 4 and the linkage means 46 are constructed in an integral piece, and therefore the greater trochanter plate 4 can be firmly secured onto the proximal part of the stem member 22 without using mechanical fitting means that connects the greater trochanter plate 4 and the linkage means 46.

The greater trochanter plate 4 attached to the femoral stem 2 of the present invention is similar to the conventional greater trochanter plate in that the greater trochanter 71 is pressed inwardly into close contact with the femur, but is greatly different in the capability to hold the top of the greater trochanter 71. When treating the greater trochanter 71 that has been severed, the greater trochanter is likely to be displaced upward before healing since the greater trochanter is repetitively pulled up by the gluteus medius musculus that is attached to the greater trochanter. According to the present invention, however, the greater trochanter 71 is effectively suppressed from being pulled up by holding the top of the greater trochanter 71, and therefore the greater trochanter 71 that has been severed can be reliably secured at the predetermined position of the femur.

The artificial hip joint 1 including the femoral stem 2 of the present invention is capable of firmly securing the greater trochanter 71 by mechanical means without the need to bore a hole in the femur. As a result, the hip joint can be loaded within several days after the replacement surgery, thus enabling the patient to leave the sickbed and start walking in the early stages of recovery.

What is claimed is:

1. A femoral stem comprising:
    a stem member including a distal part of the stem member which is adapted to be inserted in a medullary cavity of a femur and fixed therein and a proximal part of the stem member which has a neck for fixing an artificial head and is positioned at a proximal end of the distal part, the distal part and the proximal part being integrated or separable;
    a plate fixing portion which is detachably attached at a proximal-most end of the proximal part of the stem member; and
    a greater trochanter plate for depressing a greater trochanter, a proximal-most end of one side edge of the greater trochanter plate being fixed at a certain angle relative to the plate fixing portion by a fixing member that is to be located outside of the femur or the proximal-most end of the one side edge of the greater trochanter plate being fixed to the plate fixing portion so as to permit adjustment of an angle of the greater trochanter plate relative to the plate fixing portion,
    wherein the greater trochanter plate is asymmetrically configured about a longitudinal axis extending through the proximal part of the stem member such that the greater trochanter plate is elongated at the one side edge so that the one side edge of the greater trochanter plate is longer than an opposite side edge of the greater trochanter plate to provide a clearance between the plate fixing portion and a proximal-most end of the opposite side edge of the greater trochanter plate to permit passing of a tendon of a gluteus medius musculus.

2. The femoral stem according to claim 1, wherein the greater trochanter plate is composed by linking a plurality of link members in a band shape, and at least one of the link members has a through hole for passing a wire.

3. The femoral stem according to claim 2, wherein the link members are temporarily fixed to one another by screwing each link member to the its adjacent link member.

4. The femoral stem according to claim 2, wherein the fixing member is a plate setting screw.

5. The femoral stem according to claim 1, wherein the greater trochanter plate is a plate member dimensioned and shaped such that the plate member can cover an outer surface of the greater trochanter.

6. The femoral stem according to claim 5, wherein the greater trochanter plate has a claw adapted for hooking on the gluteus medius musculus which bonds to the greater trochanter.

7. The femoral stem according to claim 5, wherein the fixing member comprises:

a mating portion formed on the plate fixing portion; and a plate setting screw to be inserted into a hole formed inside the mating portion.

8. The femoral stem according to claim 7, wherein the greater trochanter plate is tightly fixed at the top of the proximal-most end of the proximal part by a taper fitting and screwing between the mating portion and the plate setting screw.

9. The femoral stem according to claim 8, wherein the greater trochanter plate has a claw adapted for hooking on the gluteus medius musculus which bonds to the greater trochanter.

10. An artificial hip joint comprising:

a femoral stem including a stem member including a distal part of the stem member which is adapted to be inserted and fixed in a medullary cavity of a femur and a proximal part of the stem member which has a neck and is positioned at a proximal end of the distal part of the stem member, the distal part and the proximal part being integrated or separable, a plate fixing portion which is detachably attached at a proximal-most end of the proximal part of the stem member, and a greater trochanter plate for depressing a greater trochanter, a proximal-most end of one side edge of the greater trochanter plate being fixed at a certain angle to the plate fixing portion by a fixing member which is to be located outside of the femur or the proximal-most end of the one side edge of the greater trochanter plate being fixed to the plate fixing portion by the fixing member so as to permit adjustment of the greater trochanter plate relative to the plate fixing portion, wherein the greater trochanter plate is asymmetrically configured about a longitudinal axis extending through the proximal part of the stem member such that the greater trochanter lapis elongated at the one side edge so that the one side edge of the greater trochanter plate is longer than an opposite side edge of the greater trochanter plate to provide a clearance between the plate fixing portion and a proximal-most end of the opposite side edge of the greater trochanter plate to permit passing of a tendon of a gluteus medius musculus;

an artificial head fixed to the neck of the proximal part; and a cup which is adapted to be fixed in an acetabulum of a pelvis and to receive the artificial head so as to compose the hip joint.

* * * * *